United States Patent [19]

Monnier et al.

[11] Patent Number: 5,138,077
[45] Date of Patent: Aug. 11, 1992

[54] SELECTIVE EPOXIDATION OF DIOLEFINS AND ARYL OLEFINS

[75] Inventors: John R. Monnier, Fairport; Peter J. Muehlbauer, Spencerport, both of N.Y.

[73] Assignee: Eastman Kodak Company, Rochester, N.Y.

[21] Appl. No.: 737,287

[22] Filed: Jul. 29, 1991

[51] Int. Cl.⁵ .................. C07D 301/10; C07D 303/04
[52] U.S. Cl. ..................................... 549/536; 502/348; 549/545
[58] Field of Search ......................................... 549/536

[56] References Cited

U.S. PATENT DOCUMENTS

| | | | |
|---|---|---|---|
| 4,039,561 | 8/1977 | Mitsuhata et al. | 260/348.34 |
| 4,169,099 | 9/1979 | Khoobiar | 260/348.34 |
| 4,248,740 | 2/1981 | Mitsuhata et al. | 549/536 |
| 4,257,967 | 3/1981 | Kajimoto | 549/536 |
| 4,267,073 | 5/1981 | Nielsen et al. | 252/455 |
| 4,389,338 | 6/1983 | Mitsuhata et al. | 252/463 |
| 4,769,358 | 9/1988 | Kishimoto et al. | 502/348 |
| 4,897,498 | 1/1990 | Monnier et al. | 549/534 |
| 4,950,773 | 8/1990 | Monnier et al. | 549/536 |

FOREIGN PATENT DOCUMENTS 25703 2/1977 Japan .................................. 549/536

*Primary Examiner*—J. E. Evans
*Attorney, Agent, or Firm*—J. Frederick Thomsen; William P. Heath, Jr.

[57] ABSTRACT

Disclosed is a process for the selective epoxidation of olefins, including diolefins, having more than 2 carbon atoms by the catalytic oxidation of such an olefin in the presence of a supported, thallium-promoted, silver catalyst.

6 Claims, No Drawings

SELECTIVE EPOXIDATION OF DIOLEFINS AND ARYL OLEFINS

This invention pertains to the selective epoxidation of diolefins and aryl olefins, especially the monoepoxidation of aliphatic diolefins. More specifically, this invention pertains to the catalytic epoxidation of such unsaturated compounds using an oxygen-containing gas and a supported, thallium-promoted, silver catalyst.

The selective oxidation of certain olefins having more than 2 carbon atoms and no allylic hydrogen atoms with an oxygen-containing gas is described in U.S. Pat. No. 4,897,498. The process disclosed in that patent is performed in the presence of a silver catalyst which may contain as promoters the residues of certain alkali metal and alkaline earth metal compounds. The patent specifically describes the preparation of 3,4-epoxy-1-butene by the monoepoxidation of butadiene with molecular oxygen in the presence of a supported, cesium-promoted, silver catalyst.

U.S. Pat. No. 4,267,073 describes a process for the production of ethylene oxide by the oxidation of ethylene with an oxygen-containing gas in the presence of catalysts comprising a porous refractory support having deposited on its exterior and interior surfaces from about 1% to 25% by weight of silver and certain amounts of thallium metal compounds. According to this patent, the use of such thallium-promoted silver catalysts in the oxidation of ethylene results in improved selectivity to ethylene oxide relative to known catalysts in general and to unpromoted silver catalysts in particular. No improvement in catalytic activity, i.e., in ethylene conversion, is mentioned in the patent.

We have discovered that certain olefins having more than 2 carbon atoms may be converted to their corresponding epoxides or monoepoxides by contacting such olefins with an oxygen-containing gas in the presence of a supported, thallium-promoted, silver catalyst. The process provided by our invention therefore comprises the preparation of the monoepoxide of an olefin selected from norbornene, norbornadiene and olefins having the general formula

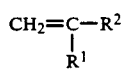  (I)

wherein $R^1$ is hydrogen or alkyl and $R^2$ is an aryl radical or the group

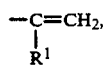

provided that the olefins of formula (I) contain more than 2 carbon atoms and do not contain any allylic hydrogen atoms, which comprises contacting the olefin with an oxygen-containing gas in the presence of a supported, thallium-promoted, silver catalyst at epoxide-forming conditions of pressure and temperature.

The catalysts used in the process of the present invention consist essentially of a catalyst support material having deposited on its surface about 1 to 30 weight percent silver and about 10 to 5000 parts per million (ppm) by weight thallium. The weight percentage silver and ppm thallium are based on the total weight of the catalyst, i.e., the finished catalyst. Although the thallium component of the catalyst may exist as a salt, oxide or hydroxide of thallium, the thallium concentration of the catalyst is based on thallium alone.

The support component of the catalysts may be selected from the large number of conventional, porous, refractory catalyst carriers or support materials which are essentially inert in the presence of the ethylenically unsaturated compound and oxygen-containing gas feeds and the products in the processes in which the catalysts are employed. Such conventional materials may be of natural or synthetic origin and preferably are of a macroporous structure, that is, a structure having a surface area below about 10 m$^2$/g. These support materials typically have an apparent porosity of greater than 20%. Supports having a siliceous and/or aluminous composition are, in general, preferred. Specific examples of suitable supports are the aluminum oxides (including the materials sold under the trade name "Alundum"), pumice, magnesia, zirconia, kieselguhr, fuller's earth, silicon carbide, porous agglomerates comprising silicon and/or silicon carbide, silica, selected clays, artificial and natural zeolites and ceramics. Refractory supports particularly useful in the preparation of the catalysts useful in the process of our invention comprise the aluminous materials, in particular those containing alpha alumina. In the case of alpha alumina-containing supports, preference is given to those having a specific surface area as measured by the B.E.T. method of from about 0.03 to 10 m$^2$/g and an apparent porosity as measured by conventional mercury or water absorption techniques of from about 25 to about 50% by volume. The B.E.T. method for determining specific surface area is described in detail in Brunauer, S., Emmett, P. H., and Teller, E., J. Am. Chem. Soc., 60, 309–16 (1938).

The following materials are specific examples of the catalyst supports which may be used.

I. Norton SN-06595, a fluidizable powder having a surface area of 0.26 m$^2$/g, a total pore volume of 0.675 cc (Hg)/gm, median pore diameter 19 microns ($\mu$), a packing density of 0.98 g/cm$^3$, and a chemical composition (weight percent) of: Al$_2$O$_3$—84.7, SiO$_2$—13.4, Fe$_2$O$_3$—0.21, TiO$_2$—0.47, CaO—0.21, MgO—0.12, Na$_2$O—0.15, K$_2$O—0.26).

II. Norton SN-08228, 0.1875 inch pellets with a surface area of 0.26 m$^2$/g, a total pore volume of 0.23 cc(Hg)/gm, median pore diameter of 19$\mu$, a packing density of 0.90 g/cm$^3$, and a chemical composition (weight percent) of: alumina—84.7, SiO$_2$—13.4, Fe$_2$O$_3$—0.21, TiO$_2$—0.47, CaO—0.21, MgO—0.12, Na$_2$O—0.15, K$_2$O—0.26.

III. Norton SA 5252, 0.1875 inch spheres with a surface area of 0.39 m$^2$/g, a total pore volume of 0.36 cc(Hg)/gm, median pore diameter of 5.4$\mu$, a packing density of 0.94 g/cm$^3$ and a chemical composition (weight percent) as follows: Al$_2$O$_3$—93.1, SiO$_2$—5.6, Fe$_2$O$_3$—0.3, TiO$_2$—0.1, CaO—0.1, MgO—0.3, Na$_2$O—0.1, K$_2$O—0.1.

IV. Norton 5552 Alumina Rings—0.25 inch rings having a surface area of 0.43 m$^2$/g, a total pore volume of 0.37 cc (Hg)/gm, a median pore diameter of 7$\mu$, a packing density of 0.80 g/cm$^3$, and a chemical composition (weight percent) of: Al$_2$O$_3$—93.1, SiO$_2$—5.6, Fe$_2$O$_3$—0.3, TiO$_2$—0.1, CaO—0.1, MgO—0.3, Na$_2$O—0.1, K$_2$O—0.1.

V. Norton SN-82501, 0.1875 inch spheres having a surface area of 0.13 m$^2$/g, a total pore volume of 0.37 cc(Hg)/gm, a median pore diameter of 32.5$\mu$, a packing density of 0.88 g/cm$^3$, and a chemical composition (weight percent) of: Al$_2$O$_3$—85.0, SiO$_2$—12.0, and the remaining 3% as Fe$_2$O$_3$, TiO$_2$, CaO, MgO, Na$_2$O and K$_2$O.

Although not preferred, other support materials which may be used include zinc oxide, e.g., having a surface area of about 3.9 m$^2$/g and a particle size of about 75–250μ; titania, e.g., having a surface area of about 0.5 m$^2$/g and a particle size of about 40–75μ; calcium oxide; silica, e.g., having a surface area of about 0.18 m$^2$/g and a particle size of about 75–250μ; barium oxide, e.g., having a surface area of about 1 m$^2$/g and a particle size of 40–75μ; boron nitride; silicon nitride; and silicon carbide.

A preferred class of support materials comprise low surface area, fused, alpha alumina supports which have relatively uniform pore diameters and are more fully characterized by having (1) B.E.T. specific surface areas of from about 0.1 m$^2$/g to about 2.0 m$^2$/g, preferably about 0.3 m$^2$/g, and (2) apparent porosities of from about 42% to about 60%, preferably from about 46% to about 58%.

The actual physical form of the catalyst support is not particularly important. While the form of the catalyst support has little effect on catalyst activity, practical considerations such as ease of heat transfer, mass transfer, pressure drop due to fluid flow restrictions, efficiency of gas-liquid-solid contacting, catalyst durability, and the like make the use of defined shapes such as spheres, pellets, extrudates, rings, saddles, and the like preferred. Conventional commercial fixed-bed reactors used in the epoxidation of ethylenically-unsaturated compounds typically are in the form of a plurality of parallel, or series of, elongated tubes (in a suitable shell). In such reactors, it is desirable to employ a support formed into a rounded shape, such as, for example, spheres, pellets, rings, tablets, and the like, having diameters of from about 0.1 inch to about 0.8 inch.

The supported, thallium-promoted, silver catalysts may be prepared according to known procedures such as those described in U.S. Pat. Nos. 4,039,561, 4,169,009, 4,267,073, 4,389,338 and 4,769,358. Thus, a thallium compound may be deposited prior to, simultaneous with or subsequent to the deposition of the silver compound.

A preferred method of preparing the catalysts from an inorganic silver compound comprises the steps of (1) forming a catalyst precursor by contacting, in either one or two steps, a porous support material with aqueous solutions of an inorganic silver compound and a thallium compound and drying the resulting impregnated support material, (2) optionally calcining the catalyst precursor wherein a gas such as air, oxygen-depleted air, nitrogen, argon, helium or the like is passed over or through the catalyst precursor at elevated temperatures, and (3) intimately contacting at a temperature of about 170° to 600° C. the catalyst precursor with a gas comprising (i) hydrogen or (ii) an inert gas containing at least 4 volume percent hydrogen. The preparation of the catalysts from an organic silver compound such as a silver amine oxalate, e.g., silver bis-ethylenediamine oxalate, comprises the steps of (1) forming a catalyst precursor by contacting, in either one or two steps, a porous support material with aqueous solutions of an organic silver compound and a thallium compound and drying the resulting impregnated support material, (2) optionally calcining the catalyst precursor wherein a gas such as air, oxygen-depleted air, nitrogen, argon, helium or the like is passed over or through the catalyst precursor at elevated temperatures, and (3) heating the catalyst precursor at a temperature of about 150° to 300° C. to thermally decompose the organic silver compound.

The catalyst precursors may be prepared employing techniques well known to those of skill in the art, such as, for example, by precipitation of suitable silver and thallium compounds on the support, by impregnation, by coprecipitation of the silver and thallium compounds and the support material, by grinding together the support material and the silver and thallium compounds in particulate form and the like. The order in which the thallium promoter is incorporated onto the support material is not critical, e.g., the support may be contacted with a silver source, then promoter, or the support may be contacted with an thallium compound, then a silver compound, or the support material may be contacted simultaneously with both a thallium compound and a silver compound.

The silver compound employed in the preparation of the catalyst precursor is not critical. Typically, the preparation of the catalyst precursor comprises impregnating the support material with a solution of a silver compound in water, an alcohol, a glycol ether, or a mixture thereof. Exemplary compounds are silver nitrate, silver oxalate, silver acetate, and the like. Those skilled in the art recognize that certain organic silver compounds require the addition of ammonia or an amine in order to solubilize the organic silver compound in an aqueous medium; thus, the use of such solvation-promoting additives is contemplated in the practice of the present invention.

The catalysts may contain about 1 to 30 weight percent silver, calculated as elemental or metallic silver and based on the total weight of active catalyst. The loading level of silver on the support preferably is within the range of about 2 up to 25 weight percent, most preferably about 5 to 20 weight percent, elemental silver. The silver typically is present in the form of uniformly-spaced, discontinuous, adherent, substantially hemispherical, discrete particles having an essentially uniform diameter of about 0.1 to 5.0μ. Catalysts bearing silver particles less than about 0.1μ give inferior catalytic results whereas silver particles larger than about 5.0μ do not appear as uniformly-spaced, discontinuous particles but appear to give a continuous layer of intergrown crystals which results in a catalyst having inferior activity due to loss of silver surface area.

The chemical form of the thallium component of the finished catalysts is not known. However, the heat and/or hydrogen treatment given to the impregnated support in the reduction of the silver salts to metallic silver most likely converts the thallium compounds or salts to an oxide or oxidic compound. The amount of thallium compound present on the catalyst support is expressed herein as the weight percent, based on the total weight of the catalyst, of thallium rather than the thallium compound. Examples of the compounds which may be used to provide the thallium component of the catalyst include thallium (I) and (III) carboxylates such as thallous formate, thallous acetate, thallic acetate, thallous malonate and thallous lactate; thallous and thallic nitrate; thallous and thallic oxide; thallium alkoxides such as thallous ethoxide; thallous carbonate; and thallous hydroxide.

The amount of thallium present on the catalyst surface may vary substantially depending, for example, on the particular support material employed and/or the surface area thereof and the amount of silver on the catalyst. Generally, the amount of thallium [Tl] on the active catalyst is in the range of about 10 to 5000 parts per million (ppm, by weight) based on the total weight of the active catalyst. The concentration of thallium preferably is in the range of about 20 to 3000 ppm with amounts in the range of about 50 to 1600 ppm (same basis) being especially preferred. Normally, the silver:-thallium weight ratio of the finished or active catalysts is in the range of about 50:1 to 4000:1, preferably in the range of about 100:1 to 2500:1, and most preferably in the range of about 100:1 to 2000:1.

Silver and thallium are the only active constituents which are added to the support materials in catalytically effective amounts. However, it is not unusual for substantial amounts, often up to about 10,000 ppm by weight of an alkali metal (usually potassium) to be present within the porous support due to (1) the use of support materials containing naturally occurring alkali metals or (2) the addition of alkali metal during support manufacture. These amounts of alkali metal present in the support in non-leachable form, rather than on the surface, do not appear to contribute to the performance of silver-thallium catalysts used in the process of this invention.

The catalyst precursor comprising a catalyst support material having the silver and thallium compounds deposited thereon as described hereinabove is converted to an active catalyst by intimately contacting the precursor, after the optional calcination step, with a gas comprising (i) hydrogen, or (ii) an inert gas containing at least about 4 volume percent hydrogen at a temperature of about 170° to 600° C. whereby the silver compound is reduced to elemental silver and the thallium metal compound is believed to be converted to an oxide and/or hydroxide. The particular conditions employed in the high temperature hydrogen treatment can vary substantially since the hydrogen concentration and temperature as well as contact times are interdependent. Alternatively, when the catalyst precursor comprises an organic silver compound, such as an amine-solubilized silver oxalate, the catalyst precursor may be converted to the active state by thermal decomposition in air at temperatures of about 150° to 300° C. Such thermal decomposition requires that the catalyst precursor be heated at a temperature and for a period of time sufficient to completely reduce the organic silver salt to metallic silver.

In the preferred procedure for preparing a highly active epoxidation catalyst, the reduction should proceed in a vigorous, fast manner by the use of an appropriate balance of temperature, hydrogen concentration in the gas, and flow rates of the reduction gas. Generally, higher concentrations of hydrogen require lower temperatures and contact times. The effectiveness of the reduction also is affected by the flow rate of the reducing gas. Thus, when a fixed bed of the catalyst precursor is subjected to the gas treatment as described above, the gas hourly space velocity (GHSV; volume of gas fed per hour per volume of catalyst precursor being treated) of the hydrogen-containing gas is in the range of about 10 to 10,000, with the optimum GHSV depending on the hydrogen content of the gas, the temperature employed and the physical form of the support material. It appears that the formation of a catalyst of superior activity requires that the reduction occur in a sharp gradient with the reduction of the silver compound occurring substantially in a quantitative manner at the leading edge of the hydrogen front. For example, we have found that if the flow rate of the gas is too fast, the reduction does not occur as a moving gradient but is spread out over a large bed distance, resulting in a catalyst which does not exhibit optimum activity. Thus, it is believed that by the use of the appropriate combination of hydrogen concentration and gas flow rates, the reduction of the silver compound occurs quantitatively, or substantially quantitatively, with substantially complete hydrogen consumption at the wavefront as it moves through the catalyst bed. Temperatures in excess of 600° C. should be avoided during the gas reduction treatment of the catalyst precursor since such can cause sintering of the elemental silver resulting in a catalyst having poor activity. Preferably, the gas treatment is carried out at temperatures not exceeding about 550° C.

The gas reduction treatment described above preferably is carried out at an initial temperature of from about 170° to 350° C. using a gas comprising an inert gas containing about 4 to 50 volume percent hydrogen. When using these temperatures and hydrogen concentration, the GHSV of the gas typically will be about 10 to 5000. The gas treatment preferably is commenced at a temperature of about 170° C. and the temperature of the bed of catalyst precursor is allowed to rise to at least 240° C., preferably to at least 350° C., by the heat generated by the reduction.

Examples of the inert gases which may be used in the gas reduction treatment include nitrogen, helium, argon, carbon dioxide, methane, or a mixture thereof. Prior to contacting the catalyst precursor with hydrogen, an inert gas may be passed over the precursor at elevated temperatures. For example, an inert gas may be passed over the catalyst precursor for 0.1 to 1 hour or longer at a gas hourly space velocity in the range of 10 to 10,000 and at temperatures of 100° to 350° C., preferably 170° to 300° C. Immediately following this pre-reduction "thermal soak", the gas feed may be changed to a hydrogen-containing gas with reduction of the silver compound commencing at about 170° C. or at the thermal soak temperature, which ever is higher. Normally, such a pre-reduction soak does not affect materially the activity/selectivity of the final catalyst.

The apparatus used in the gas reduction treatment step is not important provided that the reduction of the silver compound can be achieved as described above. For example, such apparatus may comprise a cylindrical vessel provided with means for maintaining the catalyst precursor in a fixed position and for providing uniform distribution of the gas. Such apparatus may consist of one or more reactor tubes, arranged in a parallel or series configuration, in which the catalyst, after reduction, may be used in the epoxidation of an ethylenically-unsaturated compound such as butadiene. Alternatively, the reduction apparatus may comprise an independent cylindrical vessel designed to operate solely as a reduction device.

The reduction may be carried out at pressures in the range of about 0.5 to 50 bar although the use of ambient pressure or pressures slightly above ambient give catalysts which exhibit excellent activity. Upon the completion of the hydrogen gas treatment, the catalysts thus obtained may be subjected to an extended period of gas treatment at elevated temperatures to permit the catalyst bed to achieve thermal and chemical equilibrium by removing the last traces of reduction products, e.g., water and nitrogen oxides, from the catalyst bed. This "thermal soak" typically is performed at temperatures in the range of about 300° to 400° C. using gas flow rates similar to those used in the hydrogen gas treatment, e.g. 10 to 5000 GHSV. The gas used may be the same as that used in the hydrogen gas treatment or may be an inert gas such as nitrogen.

Prior to the gas treatment-reduction procedure described hereinabove, the catalyst precursor may be subjected to a calcination procedure wherein a gas is passed over or through the catalyst precursor at a temperature of about 250° to 350° C. for about 2 to 4 hours using gas hourly space velocities in the range of about 10 to 2000. During the calcination, the silver compound is more evenly distributed in the pores and on the surface of the catalyst support material. The gas used in the calcination procedure is not critical and may be selected from air, oxygen-depleted air, inert gases such as nitrogen, argon, helium, etc. or any mixture thereof. Although it is believed not to be critical, the use of the calcination procedure is preferred since it provides a more uniform distribution of the silver and thallium compounds over the interior and exterior surfaces of the support material. Preferred calcination conditions comprise temperatures of about 300° C., times of about 2 to 4 hours and gas hourly space velocities of about 50 to 500. It will be apparent to those skilled in the art that when an organic silver salt, such as an amine-solubilized silver carboxylate salt, is used in the preparation of the catalyst precursor, then the calcination step also functions as the thermal decomposition step wherein the organic silver compound is converted to metallic silver.

The selective epoxidation process provided by this invention is carried out by contacting a gaseous mixture of norbornene, norbornadiene, or an olefin of formula (I) and an oxygen-containing gas with a supported, thallium-promoted, silver catalyst at a temperature of about 200° to 275° C. and a pressure of about 1 to 100 bar absolute. Temperatures of about 200° to 250° C. and pressures of about 1 to 2 bar absolute (approximately 1 to 2 atmospheres) constitute the preferred operating conditions. The oxygen-containing gas employed may be air, oxygen-enriched air, essentially pure oxygen or oxygen diluted with an inert gas such as helium, argon, nitrogen, etc. The volume ratio of oxygen (O$_2$) to olefin typically is in the range of about 10:1 to 1:10. To avoid the existence of explosive mixtures of oxygen and olefin and to provide for better heat transfer and kinetic control, an inert gas may be included in the gaseous feed mixture, e.g., inert gas:oxygen volume ratios in the range of about 1:1 to 10:1.

The olefin reactants which may be used in the process include norbornene, norbornadiene and olefins having the general formula

  (I)

wherein R$^1$ is hydrogen or alkyl and R$^2$ is an aryl group, a tertiary alkyl group such as tertiary butyl, tertiary amyl, or tertiary octyl, or the group having the formula

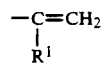

with the proviso that R$^1$ contains no hydrogen atoms in a position allylic to the ethylenic unsaturation, i.e., the <C=C> group or groups. The alkyl groups represented by R$^1$ may be unsubstituted or substituted alkyl having up to about 12 carbon atoms. Such alkyl groups preferably are unsubstituted alkyl of up to about 4 carbon atoms. When the reactant is an olefin having the formula

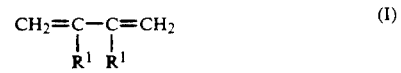  (I)

the R$^1$ substituents may be the same or different. The aryl groups represented by R$^2$ may be unsubstituted or substituted carbocyclic aryl having 6 to 10 carbon atoms, e.g., unsubstituted and substituted phenyl and naphthyl radicals. Examples of the substituents which may be present on the aryl groups include alkyl of up to about 4 carbon atoms, alkoxy of up to about 4 carbon atoms, halogen such as chloro and bromo, hydroxy, vinyl, and the like.

The epoxides produced from the olefins of formula (I) in accordance with the epoxidation process described herein have the general formula

  (II)

wherein R$^1$ and R$^2$ are defined above. The process provided by our invention is especially useful for the selective monoepoxidation of butadiene to 3,4-epoxy-1-butene The selectivity of our novel epoxidation process may be increased by performing the process in the presence of halide, typically chloride, ion. Halide ion may be provided to the process by using a thallium (I) or thallium (III) halide salt in the preparation of the catalysts. Alternatively, some or all of the halide ion may be provided to the process by including one or more organic halides in the gaseous feed. Examples of such organic halides include compounds having the formula R$^3$X wherein R$^3$ is a hydrocarbyl group or a halogenated hydrocarbyl group containing up to about 8 carbon atoms and X is a halogen atom, preferably chloro or bromo, and wherein R$^3$ contains at least one hydrogen atom which is sufficiently acidic so as to render R$^3$X capable of undergoing dehydrohalogenation under the reaction conditions. Exemplary organic halides include C$_1$ compounds such as methyl chloride, methyl bromide, methylene chloride, methylene bromide, chloroform and bromoform, and the like; C$_2$ compounds such as ethyl chloride, ethyl bromide, dichloroethane, dibromoethane, vinyl chloride, dichloroethylene, trichloroethylene, and the like; C$_3$ compounds such as dichloropropane, dibromopropane, dichloropropene, dibromopropene, and the like; C$_4$ compounds such as chlorobutane, bromobutane, dichlorobutane, dibromobutane, chlorobutene, bromobutene, dichlorobutene, dibromobutene, and the like; C$_5$ compounds such as mono-, di-, tri-, tetra-, and pentachloropentanes or pentenes, mono-, di-, tri-, tetra-, and pentabromopentanes or pentenes, cyclopentylchloride, cyclopentylbromide, and the like; C$_6$ compounds such as mono-, di-, tri-, tetra-, penta-, and hexachlorohexanes or hexenes, mono-, di-, tri-, tetra-, penta-, and hexabromohexanes or hexenes, cyclohexylchloride, cyclohexylbromide, chlorobenzene, bromobenzene, and the like; $C_7$ compounds such as chlorotoluene, bromotoluene, benzyl chloride, benzyl bromide, mono-, di-, tri-, tetra-, penta-, hexa-, and heptachloroheptanes or heptenes, mono-, di-, tri-, tetra-, penta-, hexa-, and heptabromoheptanes or heptenes, chlorocycloheptane, bromocycloheptane, and the like; $C_8$ compounds such as mono-, di-, tri-, tetra-, penta-, hexa-, hepta and octachlorooctanes or octenes, mono-, di-, tri-, tetra-, penta-, hexa-, hepta-, and octabromooctanes or octenes, and the like; as well as mixtures of any two or more thereof.

The organic halide can be added to the oxidation reaction zone in a variety of ways. For example, it can be mixed with the olefin to be oxidized and/or the oxygen-containing gas prior to contacting with the catalyst, or the organic halide can be introduced to the reaction zone separately from the feed olefin and/or the oxygen-containing gas.

The preparation of the supported, thallium-promoted, silver catalysts is illustrated by the following examples.

REFERENCE EXAMPLE 1

To a solution of silver nitrate (3.4 g) and thallium (I) nitrate (1.7 mg) in distilled water (50 mL) in a 250 mL, pear-shaped, fluted flask is added alumina powder (10.0 g, Norton SN-06595 described hereinabove) and the flask is placed on a rotary evaporator at 50° C. and tumbled at 20-30 revolutions per minute at atmospheric pressure to wet the alumina powder. The temperature of the flask is increased to 60° C. and the pressure is reduced. When the water begins to boil at reduced pressure, the vacuum is released several times to ensure complete wetting within the pores of the alumina support. The water then is removed at about 60° C. and about 0.01 to 500 torr over a period of from 0.5 to 1.0 hours.

When the rate of water collection in the rotary evaporator slows to about 1 drop every 10 seconds, the impregnated support is transferred to a drier which is placed in a forced air oven preheated to 170° C. and the impregnated support is dried for 90 minutes. The resulting catalyst precursor may be stored or calcined immediately. When the impregnated support is transferred to the drier, only the free-flowing material is processed further. The portion of material which adheres to the walls of the flask is discarded. Consequently, even though comparable amounts of silver compound and support material are employed in the Reference Examples, differences in analyzed weight percent silver result due to varying amounts of material adhering on the walls of the flask. The silver and thallium loadings reported in the Reference Examples are determined by atomic absorption elemental analysis.

The catalyst precursor prepared as described is calcined in a single pass flow reactor fabricated from Pyrex glass tubing which is 12 inches in length with an inside diameter of 0.75 inch. The catalyst precursor is maintained in place by means of a Pyrex glass frit or Pyrex glass wool. The vessel is positioned in a vertical, programmable, tube furnace and connected to a gas manifold/mass flow controller system which supplies gases to the vessel at a rate of about 100 standard cubic centimeters per minute (a gas hourly space velocity of 200 to 2000 depending on the amount of catalyst precursor in the vessel). A stainless steel-clad thermocouple is inserted in the precursor bed through the top of the vessel. The catalyst precursor is heated to 300° C. at a rate of 2 to about 10° C. per minute and held at 300° C. for 1 hour while passing a helium-oxygen mixture consisting of 20 volume percent oxygen through the catalyst precursor. The catalyst precursor then is cooled to room temperature over a period of about 30 minutes.

The calcined catalyst is reduced by changing the gas supplied by the flow controller system to a reduction gas consisting of 80 volume percent helium and 20 volume percent hydrogen. The reduction gas is passed through the catalyst bed at the rate of 100 standard cubic centimeters per minute while the furnace is heated. The reduction is monitored by the appearance and disappearance of a temperature exotherm. The furnace controller is set so that the temperature exotherm will not exceed 400° C. After the reduction is complete, the active catalyst is subjected to a thermal treatment whereby the temperature of the furnace is increased to and held at 350° C. for 1 hour before cooling to room temperature. The catalyst obtained (Catalyst I) contains 17.3 weight percent silver and 65 ppm thallium; Ag:Tl weight ratio of 2662:1.

REFERENCE EXAMPLE 2

The procedure of Reference Example 1 is repeated substantially as described using silver nitrate (3.4 g) and thallium (I) nitrate (3.5 mg) in distilled water (50 mL) and alumina powder (10.0 g, Norton SN-06595). The catalyst obtained (Catalyst II) contains 18.1 weight percent silver and 179 ppm thallium; Ag:Tl weight ratio of 1010:1.

REFERENCE EXAMPLE 3

The procedure of Reference Example 1 is repeated substantially as described using silver nitrate (3.4 g) and thallium (I) nitrate (7.0 mg) in distilled water (50 mL) and alumina powder (10.0 g, Norton SN-06595). The catalyst obtained (Catalyst III) contains 15.8 weight percent silver and 312 ppm thallium; Ag:Tl weight ratio of 506:1.

REFERENCE EXAMPLE 4

The procedure of Reference Example 1 is repeated substantially as described using silver nitrate (3.4 g) and thallium (I) nitrate (10.5 mg) in distilled water (50 mL) and alumina powder (10.0 g, Norton SN-06595). The catalyst obtained (Catalyst IV) contains 19.8 weight percent silver and 592 ppm thallium; Ag:Tl weight ratio of 334:1.

REFERENCE EXAMPLE 5

The procedure of Reference Example 1 is repeated substantially as described using silver nitrate (3.4 g) and thallium (I) nitrate (31.5 mg) in distilled water (50 mL) and alumina powder (10.0 g, Norton SN-06595). The catalyst obtained (Catalyst V) contains 17.1 weight percent silver and 1570 ppm thallium; Ag:Tl weight ratio of 109:1.

REFERENCE EXAMPLE 6

The procedure of Reference Example 1 is repeated substantially as described using silver nitrate (6.8 g) and thallium (I) nitrate (14.0 mg) in distilled water (100 mL) and silica extrusions (20.0 g, 3/16″ diameter pellets). The catalyst obtained (Catalyst VI) contains 14.8 weight percent silver and 273 ppm thallium; Ag:Tl weight ratio of 542:1.

REFERENCE EXAMPLE 7

The procedure of Reference Example 1 is repeated substantially as described using silver nitrate (3.4 g) and thallium (I) formate (6.6 mg) in distilled water (50 mL) and alumina powder (10.0 g, Norton SN-06595). The catalyst obtained (Catalyst VII) contains 16.6 weight percent silver and 340 ppm thallium; Ag:Tl weight ratio of 448:1.

REFERENCE EXAMPLE 8

The procedure of Reference Example 1 is repeated substantially as described using silver nitrate (3.4 g) and thallium (III) nitrate (10.3 mg) in distilled water (50 mL) and alumina powder (10.0 g, Norton SN-06595). The catalyst obtained (Catalyst VIII) contains 15.9 weight percent silver and 280 ppm thallium; Ag:Tl weight ratio of 568:1.

REFERENCE EXAMPLE 9

The procedure of Reference Example 1 is repeated substantially as described using silver nitrate (3.4 g) and thallium (III) acetate (10.0 mg) in distilled water (50 mL) and alumina powder (10.0 g, Norton SN-06595). The catalyst obtained (Catalyst IX) contains 14.8 weight percent silver and 337 ppm thallium; Ag:Tl weight ratio of 439:1.

REFERENCE EXAMPLE 10

The procedure of Reference Example 1 is repeated substantially as described using silver nitrate (3.4 g), thallium (I) nitrate (4.7 mg) and thallium (III) chloride (2.7 mg) in distilled water (50 mL) and alumina powder (10.0 g, Norton SN-06595). The catalyst obtained (Catalyst X) contains 18.4 weight percent silver and 345 ppm thallium; Ag:Tl weight ratio of 533:1.

REFERENCE EXAMPLE 11

The procedure of Reference Example 1 is repeated substantially as described using silver nitrate (3.4 g) and thallium (I) ethoxide (6.6 mg) in distilled water (50 mL) and alumina powder (10.0 g, Norton SN-06595). The catalyst obtained (Catalyst XI) contains 18.2 weight percent silver and 404 ppm thallium; Ag:Tl weight ratio of 450:1.

REFERENCE EXAMPLE 12

The procedure of Reference Example 1 is repeated substantially as described using a slurry of thallium (III) oxide (12.0 mg) in a solution of silver nitrate (3.4 g) in distilled water (50 mL) and alumina powder (10.0 g, Norton SN-06595). The catalyst obtained (Catalyst XII) contains 17.9 weight percent silver and 631 ppm thallium; Ag:Tl weight ratio of 284:1.

REFERENCE EXAMPLE 13

The procedure of Reference Example 1 is repeated substantially as described using a solution of silver nitrate (3.4 g) in distilled water (50 mL) and alumina powder (10.0 g, Norton SN-06595). The catalyst obtained (Catalyst XIII) contains 13.0 weight percent silver and no thallium.

The selective epoxidation process of the present invention is illustrated by the following examples using butadiene and the catalysts prepared as described above. The results reported are obtained while operating at steady state conditions using a pressure of 1 bar absolute (1 atmosphere) in a single-pass, flow reactor. The reactor tube is fabricated from Pyrex glass tubing and is 12 inches in length with an inside diameter of 0.75 inches. The catalyst charge (2-8 g) is held in place in the middle portion of the reactor tube by means of a Pyrex glass frit or glass wool. A Chromel/Alumel alloy thermocouple sheathed in stainless steel is embedded within the catalyst bed to measure reaction temperature. The reactor is heated by means of a tube furnace equipped with a proportional band controller.

The helium diluent and butadiene and oxygen are fed to the reactor in a helium:butadiene:oxygen volume ratio of 4:1:1 at a predetermined gas hourly space velocity using mass flow controllers, which permit highly accurate and reproducible flow rates of helium, butadiene and oxygen regardless of pressure changes from the supply cylinders or the reactor system downstream from the controllers. The butadiene oxidations are carried out at 225° C. unless stated otherwise.

Analyses of the reaction products and feed compositions are performed using an in-line gas sampling loop connected directly to the inlet of a Varian 3760 gas chromatograph. Both thermal conductivity (TC) and flame ionization (FI) detectors [(connected in series below the packed Chromosorb 101 column (8 ft. by 2 mm id Pyrex glass capillary column)] are used to analyze all of the reaction products. The TC detector gave quantitative analyses for oxygen, carbon dioxide, water and formaldehyde (if present), while the FI detector is used for organic molecules such as butadiene, butadiene monoxide, crotonaldehyde, 2,5-dihydrofuran, furan and acrolein. In practice, however, usually only the selective epoxidation product and olefin feedstock are present as organic molecules. Further, by means of a switching valve, it is possible to divert the feed stream through the in-line sample loop prior to passage over the catalyst. In this way, quantitative analysis of the feed stream and comparison to the corresponding data from the reactor effluent are possible, thereby providing very accurate measurements of both conversion levels and product selectivities. Output from both the TC and FI detectors are integrated using computing integrators which are programmed to give both absolute quantities and rates of formation. All reactor exit lines are heated and maintained at 125°-140° C. to prevent product condensation.

The GC analysis is performed using the following temperature programming schedule: an initial temperature of 100° C. is held for 5 minutes, followed by a temperature program rate of +10° C./minute up to a final temperature of 200° C. which is then held for 7 minutes. The helium GC carrier rate is 20 mL/min.

EXAMPLES 1-12 AND COMPARATIVE EXAMPLE 1

Butadiene is oxidized according to the above-described procedure using Catalysts I XIII, a temperature of 225° C., except in Example 10 in which a temperature of 250° C. is used, and a gas hourly space velocity of 1800. The results obtained are shown in Table I wherein CONV is the mole percent conversion of butadiene defined as:

$$\frac{\text{Moles butadiene converted to products}}{\text{Moles butadiene fed}} \times 100$$

and SELECT is the percent selectivity to 3,4-epoxy-1-butene defined as:

$$\frac{\text{Moles butadiene converted to 3,4-epoxy-1-butene}}{\text{Moles butadiene converted to total products}} \times 100$$

TABLE I

| Example | Catalyst | CONV | SELECT |
|---------|----------|------|--------|
| 1 | I | 3.5 | 85.5 |
| 2 | II | 11.8 | 86.5 |
| 3 | III | 13.5 | 88.0 |
| 4 | IV | 11.0 | 91.3 |
| 5 | V | 4.0 | 79.0 |
| 6 | VI | 3.1 | 95.0 |
| 7 | VII | 13.5 | 90.0 |
| 8 | VIII | 13.0 | 88.0 |
| 9 | IX | 5.2 | 94.0 |
| 10 | X | 8.0 | 89.0 |
| 11 | XI | 14.5 | 90.0 |
| 12 | XII | 12.5 | 91.0 |
| C-1 | XIII | 1.7 | 80.0 |

EXAMPLES 13-19 AND COMPARATIVE EXAMPLE 2

Butadiene is oxidized according to the above-described procedure using Catalysts III, VI-IX and XI-XIII, a temperature of 225° C. and a gas hourly space velocity of 900. The results obtained are shown in Table II.

TABLE II

| Example | Catalyst | CONV | SELECT |
|---------|----------|------|--------|
| 13 | III | 18.0 | 85.0 |
| 14 | VI | 3.8 | 94.0 |
| 15 | VII | 18.0 | 88.0 |
| 16 | VIII | 18.0 | 87.0 |
| 17 | IX | 6.7 | 91.0 |
| 18 | XI | 16.5 | 87.0 |
| 19 | XII | 14.6 | 89.0 |
| C-2 | XIII | 1.4 | 74.0 |

The results reported in Tables I and II demonstrate that the presence of thallium on the catalysts increases both overall conversion of the olefin and conversion of the olefin to the desired epoxide product, i.e., selectivity.

EXAMPLES 22-24

The procedure of Example 2 wherein butadiene is oxidized in the presence of Catalyst II is repeated except that 1,2-dichloroethane (DCE) is added to the feed gas to give DCE concentrations of 5, 10 and 20 parts per million by volume in the feed gas. The results obtained, as well as those obtained in Example 2, are given in Table III wherein DCE refers to the concentration (in ppm by volume) of 1,2-dichloroethane in the feed gas. These examples demonstrate the improved selectivity to 3,4-epoxy-1-butene which may be achieved by the inclusion of a halohydrocarbon in feed mixture.

TABLE III

| Example | DCE | CONV | SELECT |
|---------|-----|------|--------|
| 2 | 0 | 11.8 | 86.5 |
| 22 | 5 | 11.4 | 87.0 |
| 23 | 10 | 10.5 | 89.0 |
| 24 | 20 | 8.5 | 91.0 |

The invention has been described in detail with particular reference to preferred embodiments thereof, but it will be understood that variations and modifications may be effected within the spirit and scope of the invention.

We claim:

1. Process for the preparation of a monoepoxide of an olefin selected from norbornene, norbornadiene and olefins having the general formula $$CH_2=C-R^2 \qquad (I)$$
$$\phantom{CH_2=C-}R^1$$

wherein $R^1$ is hydrogen or alkyl and $R^2$ is an aryl group, a tertiary alkyl group or the group having the formula $$-C=CH_2$$
$$\phantom{-}R^1$$

with the proviso that $R^1$ contains no hydrogen atoms in a position allylic to the ethylenic unsaturation, which comprises contacting the olefin with an oxygen-containing gas in the presence of a supported, thallium-promoted, silver catalyst at epoxide-forming conditions of pressure and temperature, wherein the catalyst consists essentially of a catalyst support material having a surface area of less than 10 square meters per gram having distributed on the surface thereof about 1 to 30 weight percent silver and about 10 to 5000 ppm thallium.

2. Process according to claim 1 wherein the catalyst consists essentially of an alumina catalyst support material having a surface area of less than 2 square meters per gram having distributed on the surface thereof about 2 to 25 weight percent silver and about 20 to 3000 ppm thallium in a silver:thallium weight ratio of about 100:1 to 2500:1.

3. Process for the preparation of a monoepoxide of an olefin selected from norbornene, norbornadiene and olefins having the general formula $$CH_2=C-R^2 \qquad (I)$$
$$\phantom{CH_2=C-}R^1$$

wherein $R^1$ is hydrogen or alkyl and $R^2$ is an aryl group, a tertiary alkyl group or the group having the formula $$-C=CH_2$$
$$\phantom{-}R^1$$

with the proviso that $R^1$ contains no hydrogen atoms in a position allylic to the ethylenic unsaturation, which comprises contacting the olefin with an oxygen-containing gas in the presence of a supported, thallium-promoted, silver catalyst at a temperature of about 200° to 250° C., wherein the catalyst consists essentially of an alumina catalyst support material having a surface area of about 0.1 to 2 square meters per gram having distributed on the surface thereof about 5 to 20 weight percent silver and about 50 to 1600 ppm thallium.

4. Process for the preparation of 3,4-epoxy-1-butene which comprises contacting butadiene with an oxygen-containing gas in the presence of a supported, thallium-promoted, silver catalyst at epoxide-forming conditions of pressure and temperature, wherein the catalyst consists essentially of a catalyst support material having a surface area of less than 10 square meters per gram having distributed on the surface thereof about 1 to 30 weight percent silver and about 10 to 5000 ppm thallium in a silver:thallium weight ratio of about 50:1 to 4000:1.

5. Process according to claim 4 wherein the catalyst consists essentially of an alumina catalyst support material having a surface area of less than 2 square meters per gram having distributed on the surface thereof about 2 to 25 weight percent silver and about 20 to 3000 ppm thallium in a silver:thallium weight ratio of about 100:1 to 2500:1.

6. Process for the preparation of 3,4-epoxy-1-butene which comprises contacting butadiene with an oxygen-containing gas in the presence of a supported, thallium-promoted, silver-catalyst at a temperature of about 200° to 250° C., wherein the catalyst consists essentially of an alumina catalyst support material having a surface area of about 0.1 to 2 square meters per gram having distributed on the surface thereof about 5 to 20 weight percent silver and about 50 to 1600 ppm thallium in a silver:thallium weight ratio of about 100:1 to 2000:1.

* * * * *